United States Patent [19]
Klimsa

[11] 4,212,520
[45] Jul. 15, 1980

[54] EYE TESTING DEVICE

[76] Inventor: Ivan Klimsa, 3825 W. 9th St., Waterloo, Iowa 50702

[21] Appl. No.: 866,764

[22] Filed: Jan. 3, 1978

[51] Int. Cl.² .............................................. A61B 3/02
[52] U.S. Cl. ...................................... 351/37; 351/3 Z
[58] Field of Search ..................... 351/3 Z, 35, 36, 30, 351/37; 40/580; 353/68; 350/276

[56] References Cited
U.S. PATENT DOCUMENTS

| | | | |
|---|---|---|---|
| 800,521 | 9/1905 | Watson | 40/580 |
| 931,188 | 8/1909 | Ellis | 40/580 X |
| 2,231,743 | 2/1941 | Young et al. | 353/68 |
| 2,817,913 | 12/1957 | Meyer | 40/580 X |
| 3,469,904 | 9/1969 | Allen | 351/32 |

OTHER PUBLICATIONS

Luckiesh, Test Charts Representing a Variety of Visual Tasks, Mar. 1944, American Journ. of Ophth.

*Primary Examiner*—John K. Corbin
*Assistant Examiner*—Rodney Bovernick
*Attorney, Agent, or Firm*—Michael, Best & Friedrich

[57] ABSTRACT

The eye testing device for testing visual acuity includes a light-colored, opaque front chart having a plurality of cut-out openings in the shape of letters, numerals, or similar characters and a black box located behind the chart for absorbing ambient light transmitted through the cut-out openings and thereby providing a 100% contrast for the indicia or characters defined by the cut-out openings. In one embodiment, the device includes a plurality of panels or cards which vary in color intensity, e.g., from white to pitch black. Individual panels can be moved adjacent the back side of the chart to vary the degree of contrast perceived at the cut-out openings.

9 Claims, 3 Drawing Figures

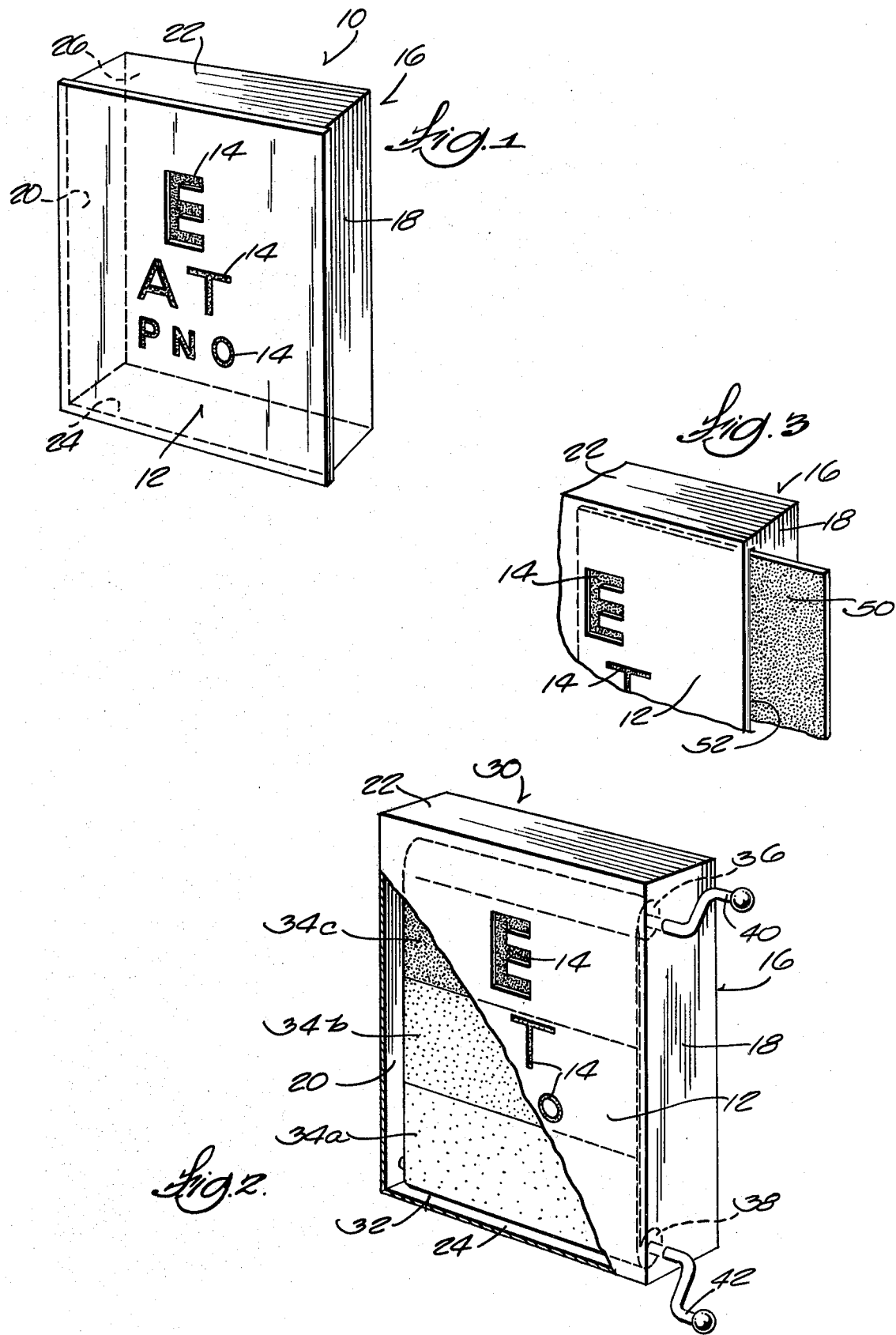

EYE TESTING DEVICE

BACKGROUND OF THE INVENTION

The invention relates generally to eye testing devices and, more particularly, to eye testing devices for testing visual acuity and including an indicia-bearing chart or panel which provides 100% contrast.

Conventional eye charts typically include graduated rows of dark-colored indicia, such as letters, numerals, or similar characters, painted or otherwise imprinted on a lighter colored panel of cardboard or the like. With age, the individual characters tend to fade at different rates. The characters do not present a 100% contrast when viewed by a patient taking an eye test because even the blackest surface does not absorb all ambient light. The contrast of individual characters can vary considerably depending upon the reflection angle of ambient light shining on the chart. This variation in contrast can affect the accuracy of the visual test, particularly for patients having a reduced ability to differentiate low contrast objects.

Representative prior art construction of other types of eye testing devices and other optical apparatus designed to test visual acuity are disclosed in the following United States Patents:

| Bechtold | 754,190 | March 8, 1904 |
| Rosenbaum | 769,805 | September 13, 1904 |
| Cross | 978,277 | December 13, 1910 |
| Freeman | 1,591,969 | July 13, 1926 |
| Allen | 3,469,904 | September 30, 1969 |

These prior art constructions do not effectively eliminate the above problems. Also, none provide a simple means for conveniently varying the degree of contrast between the characters and the background.

SUMMARY OF THE INVENTION

A principal object of the invention is to provide an eye testing device which is arranged to insure 100% contrast between the indicia or characters of an eye chart and their background irrespective of the angle of reflection of ambient light or the age of the eye chart.

Another principal object of the invention is to provide an eye testing device including the capability of selectively varying the degree of contrast between the indicia or characters and the background.

Other objects, aspects and advantages of the invention become apparent to those skilled in the art upon reviewing the following description, the drawing and the appended claims.

The invention provides an eye testing device including an opaque front panel or chart having an outer face and a plurality of cut-out openings in the form of letters, numerals, or similar characters and contrast means located behind the chart for absorbing ambient light transmitted through the cut-out openings and thereby providing 100% contrast between the cut-out openings and the outer face of the chart.

In one embodiment, the contrast means includes a box mounted on the back side of the chart and cooperating therewith to define a light-absorbing chamber which is substantially light-tight except for the cut-out openings. The interior surfaces of this box are covered with a light-absorbing material.

In another embodiment, the contrast means includes a sheet of flexible material mounted for movement behind the chart in covering relationship to the cut-out openings and including a series of colored strips of varying degree of intensity with respect to each other. The color strips are selectively moved behind the panel to vary the degree of contrast between the characters formed by the cut-out openings in the outer face of the chart, thereby providing a means for testing a patient's ability to perceive different degrees of contrast.

In another embodiment, a plurality of panels which vary in color intensities are provided for the same purpose.

BRIEF DESCRIPTION OF THE DRAWING

FIG. 1 is a perspective view of an eye testing device embodying various of the features of the invention.

FIG. 2 is a perspective, partially broken away, view of an alternate construction of the device; and FIG. 3 is a fragmentary, perspective view of still another alternate construction of the device.

Before explaining the invention in detail, it is to be understood that it is not limited in its application to the details of construction and the arrangement of components set forth in the following description or illustrated in the drawings. The invention is capable of other embodiments and being practiced and carried out in various ways. Also, it is to be understood that the phraseology and terminology employed herein is for the purpose of description and should not be regarded as limiting.

DESCRIPTION OF THE PREFERRED EMBODIMENTS

Illustrated in FIG. 1 is an eye testing device 10 embodying various of the features of the invention. The device 10 includes a light-colored, opaque front panel or chart 12 having a plurality of cut-out openings 14 in the shape of letters of the alphabet, numerals, or similar characters and arranged in the same general manner as the layout for a conventional eye chart to test visual acuity. The front chart 12 preferably is made from a thin sheet of a relatively rigid material, such as cardboard, metal or plastic, and the outer face is a white color.

Mounted behind the front chart 12 for absorbing ambient light transmitted through the cut-out openings 14 is a "black" box 16 having opposed side walls 18 and 20, opposed top and bottom walls 22 and 24, and a back wall 26. The "black" box 16 cooperates with the front chart 12 to define a substantially light-tight chamber except for the cut-out openings 14. The interior surfaces of the "black" box are coated or lined with a light-absorbing material, such as black photographic paint, black velvet, and the like, with black velvet presently being preferred. With this arrangement, a 100% contrast exists between each of the characters defined by the cut-out openings 14 and the outer face of the front chart 12 irrespective of the reflection angle of ambient light on the outer face of the chart 12.

In the alternate construction illustrated in FIG. 2, the eye testing device 30 is provided with means for selectively varying the degree of contrast between the cut-out openings 14 and the outer face of the chart 12. More particularly, a sheet 32 of paper or similar flexible material is mounted for movement closely adjacent the back side of the chart 12. The sheet 32 includes a series of colored panels or strips 34a, 34b, and 34c, of varying shades or color intensities corresponding to predetermined percentages of contrast. For example, one strip can be white and another pitch black with several intermediate strips varying in shade from very light gray to very dark gray. If the white strip is the same color as the outer face of the chart 12, it corresponds to 0% contrast while the black strip corresponds to about 95%. There usually will be some reflectance of incident light from the strips because of their close proximity to the cut-out openings 14 and, hence, the darkest strip provides less than 100% contrast. The intermediate strips can vary in shades or color intensities corresponding to intermediate percentages of contrast, e.g., 20%, 30%, 40%, etc.

In FIG. 2, each of the colored strips 34a, 34b, and 34c is shown to extend only partially behind the chart 12 for the purposes of the illustration. In actual practice, the strips usually extend substantially along the entire height of the chart 12 so that the same degree of contrast is perceived at all of the cut-out openings 14.

The opposite ends of the sheet 32 are attached to and rolled up on an upper roller 36 and a lower roller 38. The rollers 36 and 38 are rotated by respective cranks 40 and 42 to move a selective one of the strips 34a, 34b, and 34c having the desired contrast behind the cut-out openings 14. When the white strip is moved in place behind the cut-out openings 14, a patient facing the chart 12 cannot perceive the characters defined by the cut-out openings 14. In this regard, the chart 12 should be as thin as practical so as to minimize shadows at the edges of the cut-out openings 14 and the edges of the cut-out openings should be the same color as the outer face of the chart.

Patients having normal vision can begin to perceive the characters defined by the cut-out openings 14 as soon as the strip corresponding to a predetermined percentage of contrast is moved behind the chart. Patients having a reduced ability to differentiate low contrast objects will not perceive characters until a strip corresponding to a higher percentage of contrast is moved behind the cut-out openings 14.

The chart 12 preferably is removably mounted on the "black" box 16 so that the sheet 32 can be removed when it is desired to use the device 30 for eye tests. The "black" box 16 can be omitted completely so long as some type of colored contrast means, either stationary or adjustable as in the construction illustrated in FIGS. 2 and 3, is located behind the chart 12 and covers the cut-out openings 14. However, the use of a "black" box is preferred for devices to be used for a normal eye test because of the capability of providing substantially 100% contrast irrespective of the reflection angle of ambient light or the age of the device.

In the alternate construction illustrated in FIG. 3, a plurality of colored panels or cards 50 (one shown) are used in place of a multiple-strip sheet. The outer surfaces of the individual cards 50 vary in color intensity to provide a different predetermined percentage of contrast when placed behind the chart 12 to cover the cut-out openings 14. A card 50 of the desired contrast is inserted through a slot 52 provided in one of the walls of the 37 black box 16, e.g., the side wall 18. The slot 52 preferably is covered when the device is being used for eye tests so as to prevent the entrance of ambient light except through the cut-out openings 14. For example, a spring-loaded trap door (not shown) can be provided for this purpose. As with the construction illustrated in FIG. 2, the "black" box can be omitted.

I claim:

1. An eye testing device including a front chart having a light-colored, opaque outer face and a plurality of cut-out openings in the shape of letters, numerals, or similar characters; and contrast means located behind said chart and having an opaque surface of a color darker than that of the outer face of said chart for absorbing ambient light transmitted in a direction toward the outer face of said chart and through said cut-out openings to provide a contrast between said cut-out openings and the outer face of said chart, said contrast means includes a box mounted on the back side of said chart and cooperating therewith to define a light-absorbing chamber which is substantially closed except for said cut-out openings, the interior surfaces of said box being covered with a light-absorbing material.

2. An eye testing device according to claim 1 wherein said chart is formed from a relatively thin sheet material so as to minimize shadows at the edge of said cut-out openings.

3. An eye testing device according to claim 1 wherein said light-absorbing material is black velvet.

4. An eye testing device according to claim 2 wherein said contrast means comprises contrast adjustment means including a plurality of opaque sections which vary in color intensity relative to each other and absorb different amounts of ambient light, said sections being adapted for removable placement behind the back side of said chart in covering relationship to said cut-out openings.

5. An eye testing device according to claim 4 wherein said contrast adjustment means includes a sheet of material mounted for movement behind said chart in covering relationship to said cut-out openings and including a series of opaque colored strips of varying degree of ambient light absorbtivity; and means for selectively moving said strips into place behind said chart.

6. An eye testing device according to claim 5 wherein said sheet is a flexible material having opposite ends;

said last-mentioned means includes an upper and a lower roller mounted adjacent the back side of said chart for relative rotation with the opposite ends of said flexible material being attached to said rollers to be rolled thereupon; and means for rotating said rollers and thereby moving a selected one of said strips into place behind said chart.

7. An eye testing device according to claim 4 wherein said color adjustment means includes a plurality of panels, each having an opaque outer surface having ambient light absorbtivity which differs from that another of said panels; and means for removably mounting individual of said panels with the outer surface thereof located closely adjacent the back side of said chart in covering relationship to said cut-out openings.

8. An eye testing device according to claim 4 wherein the outer surface of one of said sections is of a light color and corresponds to substantially 0% contrast with respect to the outer face of said chart;

the outer surface of another of said sections is a dark color and corresponds to substantially 95% contrast with respect to the outer face of said chart; and the outer surface of still another of said sections is an intermediate color and corresponds to an intermediate percentage of contrast with respect to the outer face of said chart.

9. An eye testing device according to claim 8 wherein the outer face of said chart and the outer face of said one section is white, the outer surface of said another section is black, and the outer surface of said still another section is gray.

* * * * *